United States Patent
Lahti et al.

(10) Patent No.: US 11,972,845 B2
(45) Date of Patent: *Apr. 30, 2024

(54) MACRO-BASED DIAGNOSES FOR ANATOMIC PATHOLOGY

(71) Applicant: Cerebrum Corporation, Chandler, AZ (US)

(72) Inventors: Gregg Lahti, Gilbert, AZ (US); Matthew Hoppes, Phoenix, AZ (US); Michael Howell, Chandler, AZ (US); Brandon Sleater, Gilbert, AZ (US)

(73) Assignee: Cerebrum Holding Corporation, Chandler, AZ (US)

( * ) Notice: Subject to any disclaimer, the term of this patent is extended or adjusted under 35 U.S.C. 154(b) by 513 days.

This patent is subject to a terminal disclaimer.

(21) Appl. No.: 16/142,356

(22) Filed: Sep. 26, 2018

(65) Prior Publication Data

US 2019/0103170 A1    Apr. 4, 2019

Related U.S. Application Data

(60) Provisional application No. 62/565,320, filed on Sep. 29, 2017.

(51) Int. Cl.
*G16H 10/40* (2018.01)
*G16H 15/00* (2018.01)
*G16H 50/20* (2018.01)
*G16H 30/20* (2018.01)

(52) U.S. Cl.
CPC ............ *G16H 10/40* (2018.01); *G16H 15/00* (2018.01); *G16H 50/20* (2018.01); *G16H 30/20* (2018.01)

(58) Field of Classification Search
CPC ........ G16H 10/40; G16H 50/20; G06F 19/30; G06F 19/32; G06F 19/34; G06F 19/36; G06Q 50/22; G06Q 50/24
See application file for complete search history.

(56) References Cited

U.S. PATENT DOCUMENTS

| | | |
|---|---|---|
| 2003/0177041 A1 | 9/2003 | Millican, III |
| 2004/0030583 A1 | 2/2004 | Fleming |
| 2009/0222746 A1 | 9/2009 | Chirica et al. |
| 2009/0234671 A1* | 9/2009 | Jones ............ G16H 70/60 705/2 |
| 2009/0316977 A1 | 12/2009 | Juncker et al. |
| 2010/0332456 A1 | 12/2010 | Prahlad et al. |

(Continued)

*Primary Examiner* — Mamon Obeid
*Assistant Examiner* — Chance L Smith
(74) *Attorney, Agent, or Firm* — Procopio, Cory, Hargreaves & Savitch LLP; Pattric J. Rawlins

(57) ABSTRACT

A client device presents a user interface including a macro entry field for defining a macro indicator from a plurality of macro indicators and transmits the macro indicator. A server stores a database of macro-based diagnoses, each macro-based diagnosis associated with one or more elements of an accession, and one or more specimens associated with the accession. The server also receives the macro indicator from the client device, retrieves an initial diagnosis from the database of macro-based diagnoses responsive to the macro indicator, and transmits the initial diagnosis. The client device, receives the initial diagnosis, pre-populates one or more text boxes on the user interface with information from the initial diagnosis, and enables the user to edit the pre-populated one or more text boxes.

20 Claims, 9 Drawing Sheets

(56) References Cited

U.S. PATENT DOCUMENTS

| | | |
|---|---|---|
| 2011/0060766 A1 | 3/2011 | Ehlke |
| 2011/0093445 A1* | 4/2011 | Rundell ................. G16H 40/20 707/705 |
| 2012/0072452 A1 | 3/2012 | Stratman et al. |
| 2012/0197660 A1* | 8/2012 | Prodanovich .......... G16H 10/40 235/494 |
| 2013/0085798 A1 | 4/2013 | Spatola et al. |
| 2013/0179183 A1* | 7/2013 | Wagner .............. G06Q 10/0637 705/2 |
| 2013/0246488 A1* | 9/2013 | Weinschenk ............ G06F 16/22 707/825 |
| 2013/0311936 A1 | 11/2013 | Lahti et al. |
| 2016/0283839 A1* | 9/2016 | Ye .......................... G16H 15/00 |
| 2019/0122750 A1* | 4/2019 | Ghosh .................... G16H 10/60 |

* cited by examiner

*FIG. 5*

MACRO-BASED DIAGNOSES FOR ANATOMIC PATHOLOGY

CROSS-REFERENCE TO RELATED APPLICATION

This application claims the benefit under 35 U.S.C. § 119(e) of U.S. Provisional Patent Application Ser. No. 62/565,320, filed Sep. 29, 2017, the disclosure of which is hereby incorporated herein in its entirety by this reference.

This application is also related to U.S. patent application Ser. No. 16/142,390, filed concurrently with this application and entitled "Configurable Workflow for Pathology Labs," which claims the benefit under 35 U.S.C. § 119(e) of U.S. Provisional Patent Application Ser. No. 62/565,329, filed Sep. 29, 2017, the disclosures of which are hereby incorporated herein in their entirety by this reference.

TECHNICAL FIELD

Embodiments of the present disclosure relate generally to managing laboratory information and more specifically to the application of directing work by automating parts of the generation, modification, presentation, and input of information in a user interface for anatomic pathology laboratory operation.

BACKGROUND

In an anatomic pathology lab, human or animal tissue is processed through various methods to achieve a thin slice of stained tissue on a slide. In general, the operational work done on a specimen goes from one step or station to another in a sequence. These steps are related to the work being done on the specimen to create a final product of the stained tissue on the slide. A Pathologist may have multiple slides per specimen, which usually means one or more tests done on the specimen and multiple specimens per accession (i.e., patient case). As a result, a Pathologist may look at hundreds of slides per day when performing diagnoses. The Pathologist needs a faster and more automated way of entering diagnosis data about the test on the tissue performed and what their ultimate diagnosis would be for each of the specimens being presented on an accession.

BRIEF DESCRIPTION OF THE DRAWINGS

FIG. 5 shows a screenshot of information that may be presented to a Pathologist for editing.

DETAILED DESCRIPTION

Figure 1:
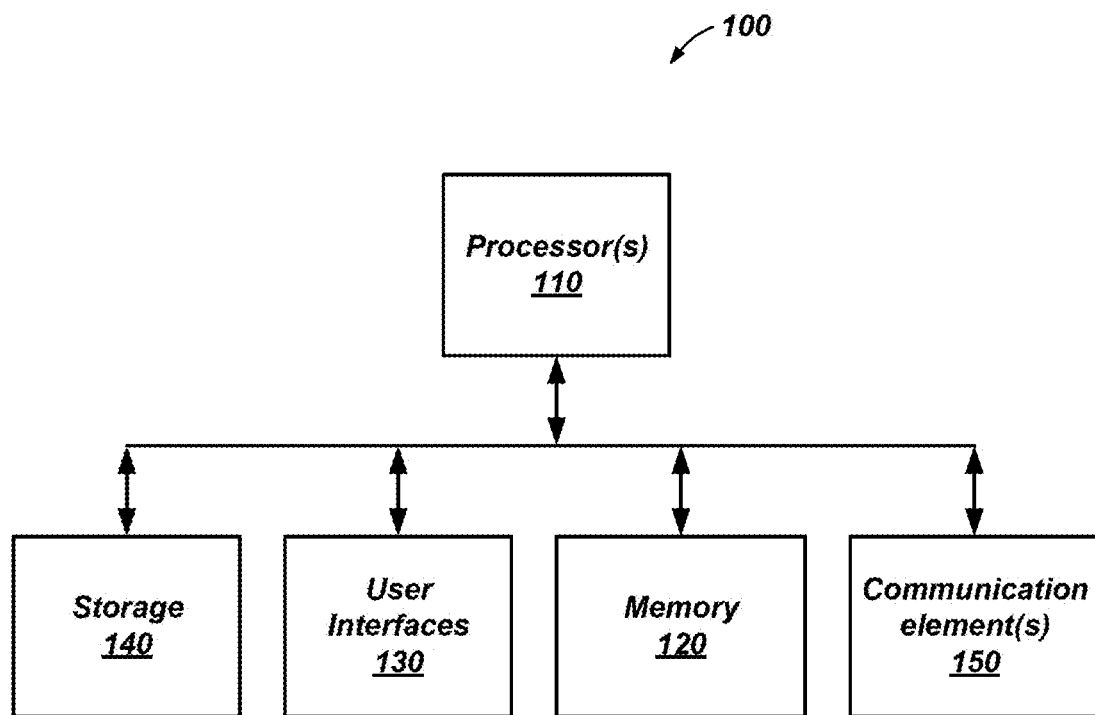
FIG. 1 illustrates a computing system for practicing embodiments of the present disclosure.

In the following description, reference is made to the accompanying drawings in which is shown, by way of illustration, specific embodiments in which the disclosure may be practiced. The embodiments are intended to describe aspects of the disclosure in sufficient detail to enable those skilled in the art to practice the invention. Other embodiments may be utilized and changes may be made to the disclosed embodiments without departing from the scope of the disclosure. The following detailed description is not to be taken in a limiting sense, and the scope of the present invention is defined only by the appended claims.

Furthermore, specific implementations shown and described are only examples and should not be construed as the only way to implement the present disclosure unless specified otherwise herein. It will be readily apparent to one of ordinary skill in the art that the various embodiments of the present disclosure may be practiced by numerous other partitioning solutions.

In the following description, elements, circuits, and functions may be shown in block diagram form in order not to obscure the present disclosure in unnecessary detail. Conversely, specific implementations shown and described are exemplary only and should not be construed as the only way to implement the present disclosure unless specified otherwise herein. Additionally, block definitions and partitioning of logic between various blocks is exemplary of a specific implementation. It will be readily apparent to one of ordinary skill in the art that the present disclosure may be practiced by numerous other partitioning solutions. For the most part, details concerning timing considerations and the like have been omitted where such details are not necessary to obtain a complete understanding of the present disclosure and are within the abilities of persons of ordinary skill in the relevant art.

Those of ordinary skill in the art would understand that information and signals may be represented using any of a variety of different technologies and techniques. For example, data, instructions, commands, information, signals, bits, symbols, and chips that may be referenced throughout this description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the present disclosure may be implemented on any number of data signals including a single data signal.

The various illustrative logical blocks, modules, and circuits described in connection with the embodiments disclosed herein may be implemented or performed with a general purpose processor, a special purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A general-purpose processor may be considered a special-purpose processor while the general-purpose processor is configured to execute instructions (e.g., software code) related to embodiments of the present disclosure. A processor may also be implemented as a combination of computing devices, such as a combination of a DSP and a microprocessor, a plurality of microprocessors, one or more microprocessors in conjunction with a DSP core, or any other such configuration.

Also, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a thread, a function, a procedure, a subroutine, a subprogram, etc. Furthermore, the methods disclosed herein may be implemented in hardware, software, or both. If implemented in software, the functions may be stored or transmitted as one or more instructions or code on computer-readable media. Computer-readable media includes both computer storage media and communication media including any medium that facilitates transfer of a computer program from one place to another.

In some embodiments, some or all of the features described herein are implemented within a computer processor or processing device that executes software procedures. The transformation of data that occurs according to the specific procedures of embodiments described herein render the processing device executing such embodiments as a special-purpose processing device capable of new functionality that is otherwise not available executing conventional software or logical procedures. In addition, efficient processing of such procedures requires implementation within computer processing systems. Furthermore, the interactions between an electronic storage device to store data associated with the techniques described herein and the computer processing devices to execute the techniques described herein achieve much greater efficacy than would be possible through other non-computerized means.

For at least these reasons, various embodiments of the present disclosure, as described more fully herein, provide a technical solution to one or more problems that arise from technology that could not reasonably be performed by a person, and various embodiments disclosed herein are rooted in computer technology in order to overcome the problems and/or challenges described below. Further, at least some embodiments disclosed herein may improve computer-related technology by allowing computer performance of a function not previously performable by a computer.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. In addition, unless stated otherwise, a set of elements may comprise one or more elements.

Elements described herein may include multiple instances of the same element. These elements may be generically indicated by a numerical designator (e.g. 110) and specifically indicated by the numerical indicator followed by an alphabetic designator (e.g., 110A) or a numeric indicator preceded by a "dash" (e.g., 110-1). For ease of following the description, for the most part element number indicators begin with the number of the drawing on which the elements are introduced or most fully discussed. Thus, for example, element identifiers on a FIG. 1 will be mostly in the numerical format 1xx and elements on a FIG. 4 will be mostly in the numerical format 4xx.

Headings may be included herein to aid in locating certain sections of detailed description. These headings should not be considered to limit the scope of the concepts described under any specific heading. Furthermore, concepts described in any specific heading are generally applicable in other sections throughout the entire specification.

Reference throughout this specification to "one embodiment," "an embodiment," or similar language means that a particular feature, structure, or characteristic described in connection with the indicated embodiment is included in at least one embodiment of the present disclosure. Thus, the phrases "in one embodiment," "in an embodiment," and similar language throughout this specification may, but do not necessarily, all refer to the same embodiment.

Before describing specific embodiments, and in order to facilitate description in the present disclosure, various terms are described herein. Where ambiguity may exist between the plain meaning, dictionary meaning, and the term as described herein, a person of ordinary skill in the art will recognize the term as described herein will best conform to a more comprehensive understanding of embodiments of the present disclosure.

As used herein, unless referred to specifically with a different meaning, an "accession" is a test or group of tests ordered for a particular specimen received by a lab or other health care service.

As used herein, the term "substantially" in reference to a given parameter, property, or condition means and includes to a degree that one of ordinary skill in the art would understand that the given parameter, property, or condition is met with a small degree of variance, such as, for example, within acceptable manufacturing tolerances. By way of example, depending on the particular parameter, property, or condition that is substantially met, the parameter, property, or condition may be at least 90% met, at least 95% met, or even at least 99% met.

As used herein the term "module" means a software process, a collection of software processes, a collection of hardware elements, or a combination thereof configured to implement one or more elements of the present disclosure.

Some drawings presented herein include depictions of a Graphical User Interface (GUI), which may include color elements. Embodiments of the present disclosure address issues such as lab accuracy and lab efficiency. As such, formatting and colors associated with certain elements may be useful for increasing efficiency and accuracy by assisting a user with performing tasks related to presentation and modification of information related to embodiments of the present disclosure.

Description may be presented herein to a software application referred to as Labdivus, Labdivus application, Labdivus product, or Labdivus software. These references are to a specific software product including embodiments of the present disclosure. A person of ordinary skill in the art will readily understand that embodiments of the present disclosure may be included in many different software applications and software products and Labdivus is merely being used as an example of one specific product including embodiments of the present disclosure.

FIG. 1 illustrates a computing system 100 for practicing embodiments of the present disclosure. The computing system 100 may be a user-type computer, a file server, a compute server, or other similar computer. Computer, computing system, and server may be used interchangeably herein to indicate a system for practicing embodiments of the present disclosure. The computing system 100 is configured for executing software programs containing computing instructions and includes one or more processors 110, memory 120, one or more communication elements 150, user interface elements 130, and storage 140.

As non-limiting examples, the computing system 100 may be a user-type computer, a file server, a compute server, a notebook computer, a tablet, a handheld device, a mobile device, or other similar computer system for executing software.

The one or more processors 110 may be configured for executing a wide variety of operating systems and applications including the computing instructions for carrying out embodiments of the present disclosure.

The memory 120 may be used to hold computing instructions, data, and other information for performing a wide variety of tasks including performing embodiments of the present disclosure. By way of example, and not limitation, the memory 120 may include Synchronous Random-Access Memory (SRAM), Dynamic RAM (DRAM), Read-Only Memory (ROM), Flash memory, and the like.

Information related to the computing system 100 may be presented to, and received from, a user with one or more user interface elements 130. As non-limiting examples, the user interface elements 130 may include elements such as displays, keyboards, mice, joysticks, haptic devices, microphones, speakers, cameras, and touchscreens. A display on the computing system 100 may be configured to present a graphical user interface (GUI) with information about the embodiments of the present disclosure, as is explained below.

The communication elements 150 may be configured for communicating with other devices or communication networks. As non-limiting examples, the communication elements 150 may include elements for communicating on wired and wireless communication media, such as for example, serial ports, parallel ports, Ethernet connections, universal serial bus (USB) connections IEEE 1394 ("firewire") connections, BLUETOOTH® wireless connections, 802.1 a/b/g/n type wireless connections, and other suitable communication interfaces and protocols.

The storage 140 may be used for storing relatively large amounts of non-volatile information for use in the computing system 100 and may be configured as one or more storage devices. By way of example, and not limitation, these storage devices may include computer-readable media (CRM). This CRM may include, but is not limited to, magnetic and optical storage devices such as disk drives, magnetic tapes, CDs (compact disks), DVDs (digital versatile discs or digital video discs), and other equivalent storage devices.

Software processes illustrated herein are intended to illustrate representative processes that may be performed by the systems illustrated herein. Unless specified otherwise, the order in which the process acts are described is not intended to be construed as a limitation, and acts described as occurring sequentially may occur in a different sequence, or in one or more parallel process streams. It will be appreciated by those of ordinary skill in the art that many steps and processes may occur in addition to those outlined in flow charts. Furthermore, the processes may be implemented in any suitable hardware, software, firmware, or combinations thereof.

When executed as firmware or software, the instructions for performing the processes may be stored on a computer-readable medium. A computer-readable medium includes, but is not limited to, magnetic and optical storage devices such as disk drives, magnetic tape, CDs (compact disks), DVDs (digital versatile discs or digital video discs), and semiconductor devices such as RAM, DRAM, ROM, EPROM, and Flash memory.

By way of non-limiting example, computing instructions for performing the processes may be stored on the storage 140, transferred to the memory 120 for execution, and executed by the processors 110. The processors 110, when executing computing instructions configured for performing the processes, constitutes structure for performing the processes and can be considered a special-purpose computer when so configured. In addition, some or all portions of the processes may be performed by hardware specifically configured for carrying out the processes.

Using a computing system 100 with a graphical operating system, embodiments of the present disclosure include software application tools providing functional panels or windows within the application to segment the functionality. Many panels can be used to describe multiple functions but in this description two of the panels will be presented to the user which control and display the items being utilized within the application tool (also referred to herein as "application software" and a "macro-based diagnosis tool"). The application tool is used to create digital content for various products of which one element could be to generate a GUI (Graphical User Interface) to run on a computing system 100 utilizing an LCD touch/display screen. In this application tool, the user provides graphical data in the form of images, pictures, and text to create a digital content output. The digital content output could be represented on a computer screen or hardware screen or output to paper.

In an anatomic pathology lab, human or animal tissue is processed through various methods to achieve a very thin slice, for example 2 micron thick, of stained tissue on a slide. The Pathologist must view, or read, the slide with stained tissue on it to determine potential illnesses and issues. Each of these slides read usually represents a specific test done on the specimen. The Pathologist may have multiple slides per specimen which usually means one or more tests done on the specimen and multiple specimens per accession, or patient case. A Pathologist may look at a total of hundreds of slides per day when performing diagnoses. The Pathologist needs a fast way of entering diagnosis data about the test on the tissue performed and what their ultimate diagnosis would be for each of the specimens being presented on an accession.

Pathologists are an expensive part of the overall process of diagnoses of a patient and diagnosis accuracy is the top priority of the Pathologist. To accommodate a large workload, be efficient, and be accurate in the diagnosis, the Labdivus application creates a macro-based diagnosis tool to aid the Pathologist in selecting the diagnosis for the specimen. The macro-based diagnosis tool in the Labdivus product uses a macro indicator (i.e., a macro name) to identify the diagnosis type that will be used to generate pathology lab diagnoses. Generally, 80% of each type of diagnoses across each type of specimen is usually the same. For example, when diagnosing a colon polyp, there can be a dozen type of diagnoses that could be presented and for routine polypectomies that are benign they get one diagnosis of the dozen. The Pathologist, knowing that it's a polyp, can quickly utilize a macro to get the polyp-related set of diagnoses and then narrow it down to the diagnosis that identifies the polyp as benign. The macro provides a templated data entry for the diagnosis text, microscopic text, and comment text. The macro system provides several benefits: 1) a quick way to enter templated text for the pathology report, 2) standardizes the complete texts used for each diagnosis type across all accessions and 3) ensures regulation guideline requirements that each specimen gets the correct diagnosis components needed for the pathology report. The macro system also ensures correct International Classification of Diseases (ICD) codes as well as Current Procedural Terminology (CPT) codes can be applied to the specimen diagnosis at macro selection time to ensure correct insurance identification and billing code selection is used for each specimen.

Figure 2:
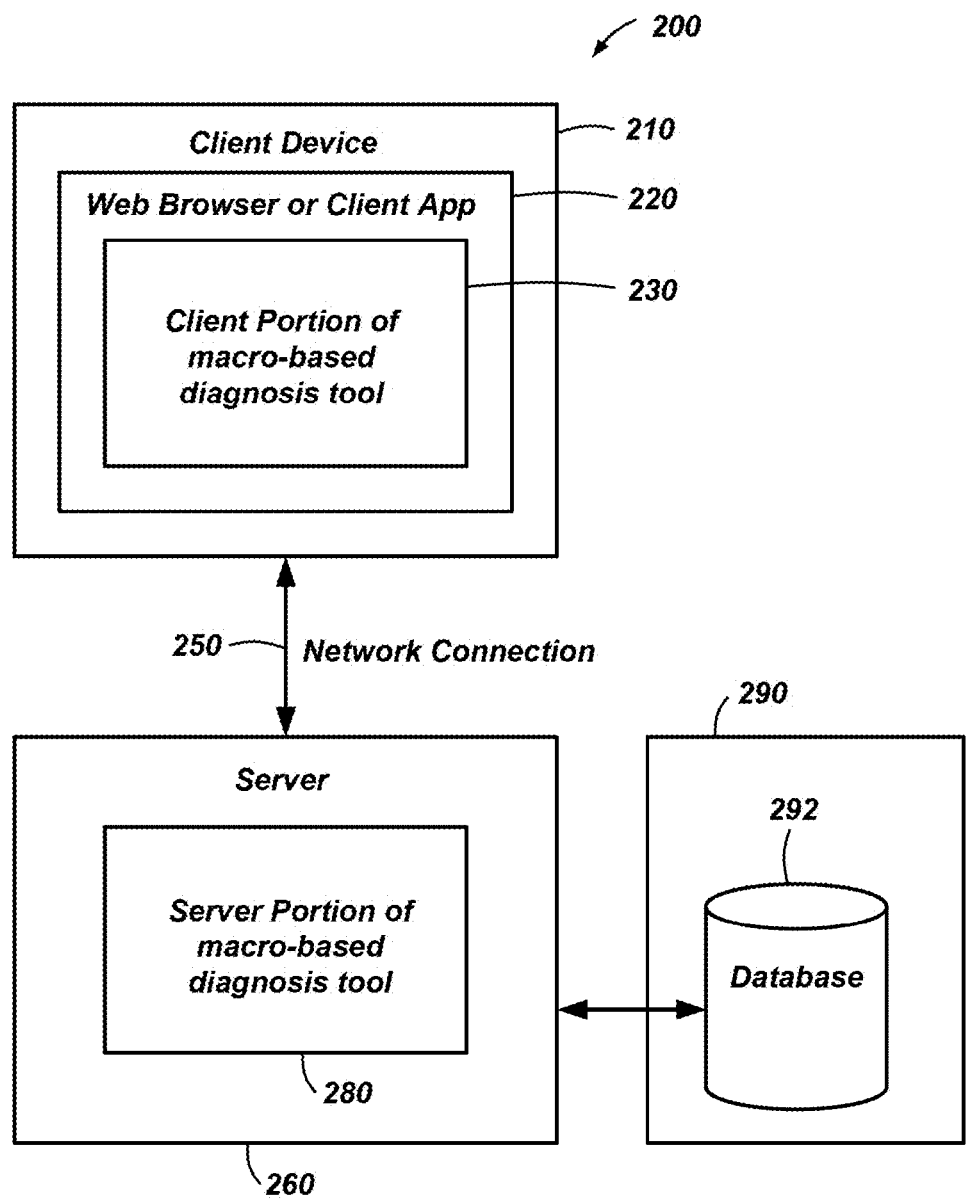
FIG. 2 shows a system for managing, entering, and presenting information for creating a software application for a macro-based diagnosis tool.

FIG. 2 shows a system for managing, entering, and presenting information for creating a software application for the macro-based diagnosis tool 200. In FIG. 2, the software application organization is shown at a high level where a client portion 230 of the macro-based diagnosis tool 200 executes in a web browser or client application 220 on a client device 210. The client device 210 connects to a server 260 through a network connection 250. A server portion 280 of the macro-based diagnosis tool 200 executes on the server 260 and connects to a database server 290 for application variable storage. The database server 290 includes a database of macro-based diagnoses 292, each macro-based diagnosis associated with one or more elements of an accession, and one or more specimens associated with the accession. Of course, the server 260 and the database server 290 may be different physical devices or the same physical device. In addition, the client portion 230 may execute directly on the client device 210 without the need for the web browser 220. As a non-limiting example, the client portion 230 may be supplied as a stand-alone application (often referred to as an "App") configured for execution on a portable device or other suitable user device.

Figure 3:
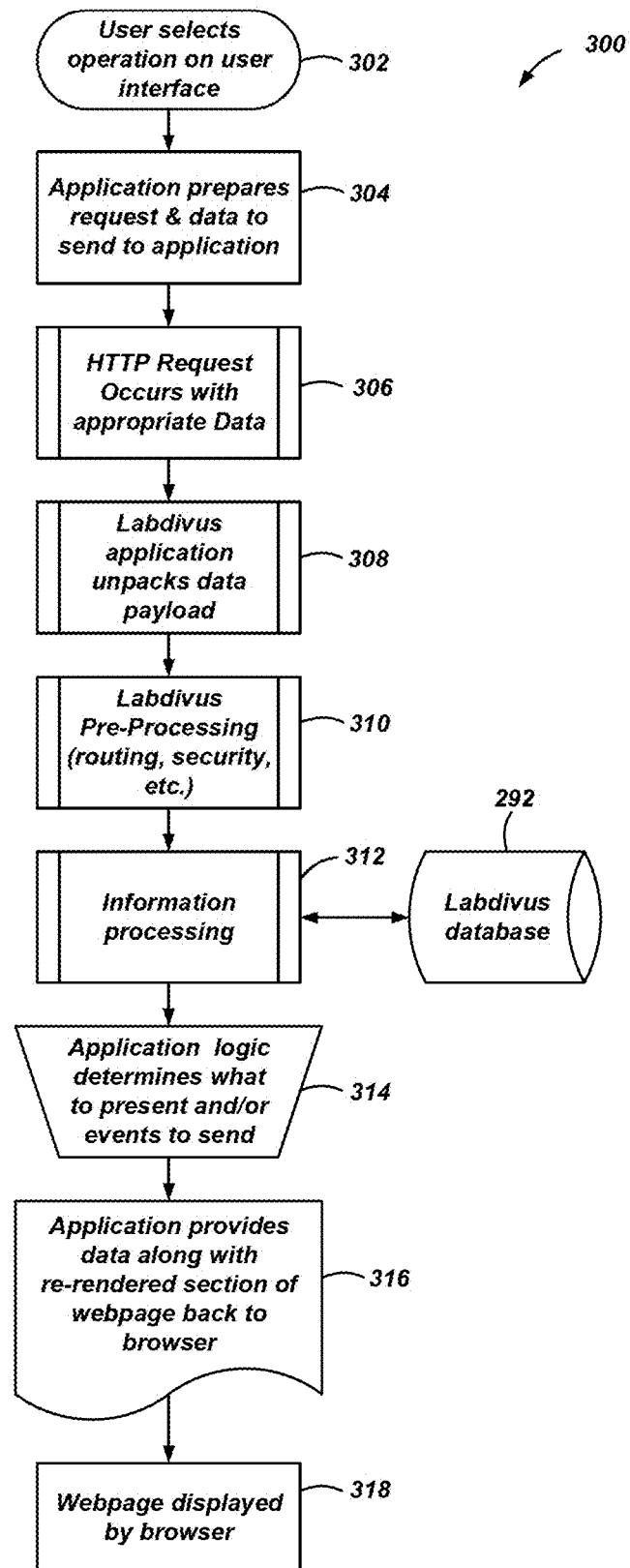
FIG. 3 is a flow chart illustrating some processes of the application software.

FIG. 3 is a flow chart illustrating some processes 300 for execution of the application software. With reference to FIGS. 2 and 3, the application software may be configured to utilize a standard web browser 220 as the front-end view to the user. The web browser 220 is the client of the server 260 and thus the server portion 280 of the application software running on the server 260. As stated earlier, rather than using a web browser 220, some embodiments may use a stand-alone application as the client portion 230 of the application software running on the client device 210.

At process block 302, the user selects an operation to be performed on the user interface presented on the client device 210.

At process block 304, the request and data appropriate for the given selection made by the user is prepared for communication. The communication between the client device 210 and the server 260 utilizes standard supported protocols (HTTP/HTTPS).

At process block 306, the client device 210 makes an HTTP request to the server 260 with the appropriate data payload. The Labdivus application running on the server 260 provides the business logic and supplies the client device 210 with the GUI (graphical user interface) that the user sees At process block 308, the Labdivus application running on the server 260 unpacks the data payload from the HTTP request and at process block 310 the application performs any appropriate routing and security processes.

At process block 312, the Labdivus application performs the information processing to examine the request data, access the database 292 to retrieve relevant diagnosis data, and perform any desired processing of the data. As part of this process, the application running on the server 260 connects to the database server 290, which contains information about how to run the application, holds variables and other information regarding the operation of the Labdivus application, and stores information that the client device 210 provides.

At process block 314, once the information is completely processed and data has been exchanged with the database server 290, the application on the server 260 prepares the data to be presented along with any appropriate events to send to the client device 210.

At process block 316, the application sends the data along with a re-rendered section of the user interface back to the client device 210 for presentation and at process block 318 the new information is presented on the client device 210.

Figure 4:
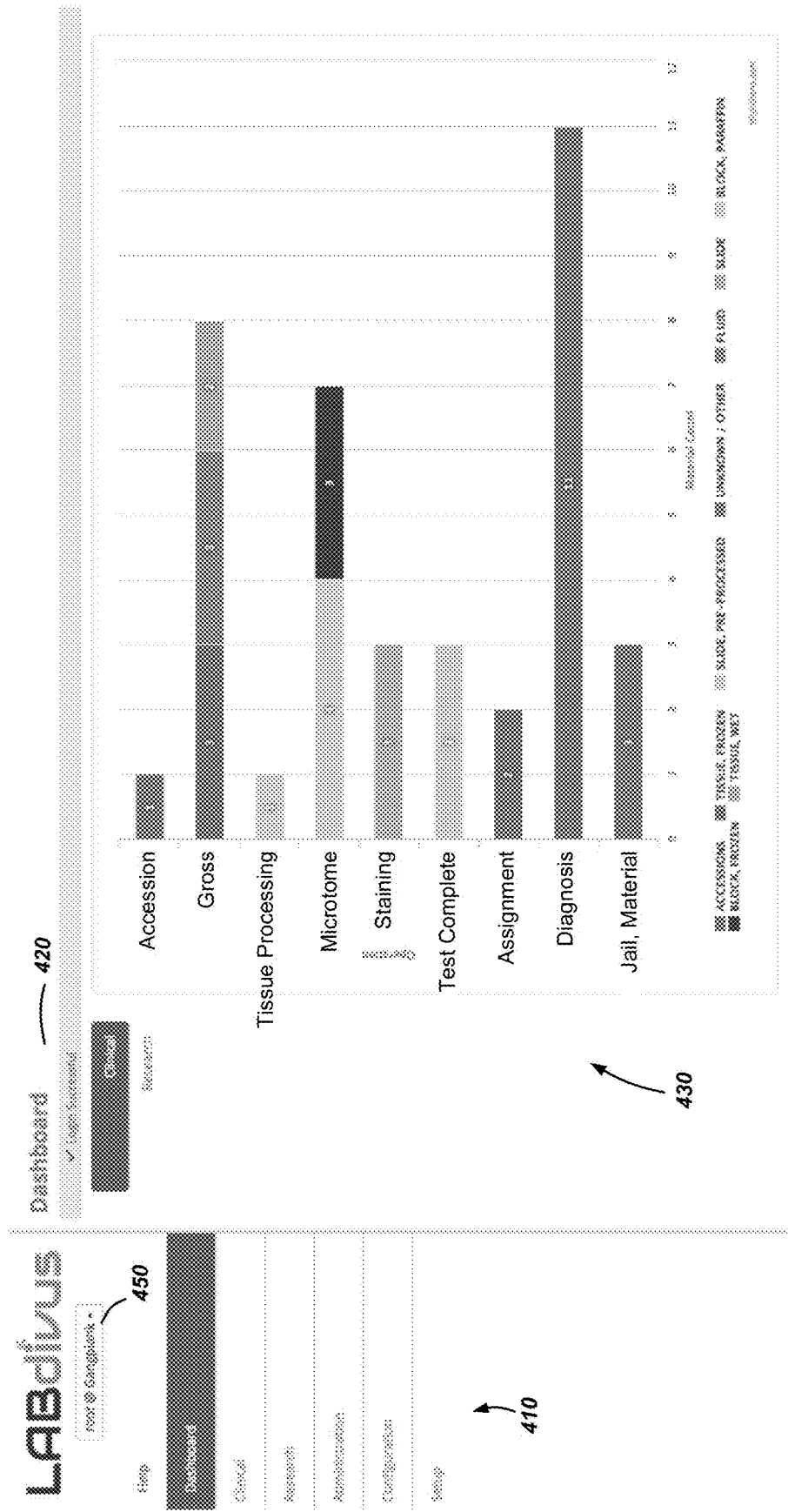
FIG. 4 shows a screenshot of the software application setup for an anatomic pathology lab tool.

FIG. 4 shows a screenshot on the client device 210 of the software application setup for an anatomic pathology lab tool. A navigation indicator 420 is shown along the top side of the window with the text "Dashboard" displayed as the current navigation location. A user login indicator 450 shows the current user and may be configured as a selection element (e.g., a dropdown box) to change to a different user. A menu 410 shows the various operations that a user can perform from this window. An information window 430 illustrates various operations and elements, such as, for example, accession, tissue processing, microtome, and staining are show, as well as various processes within these operations.

Figure 5:
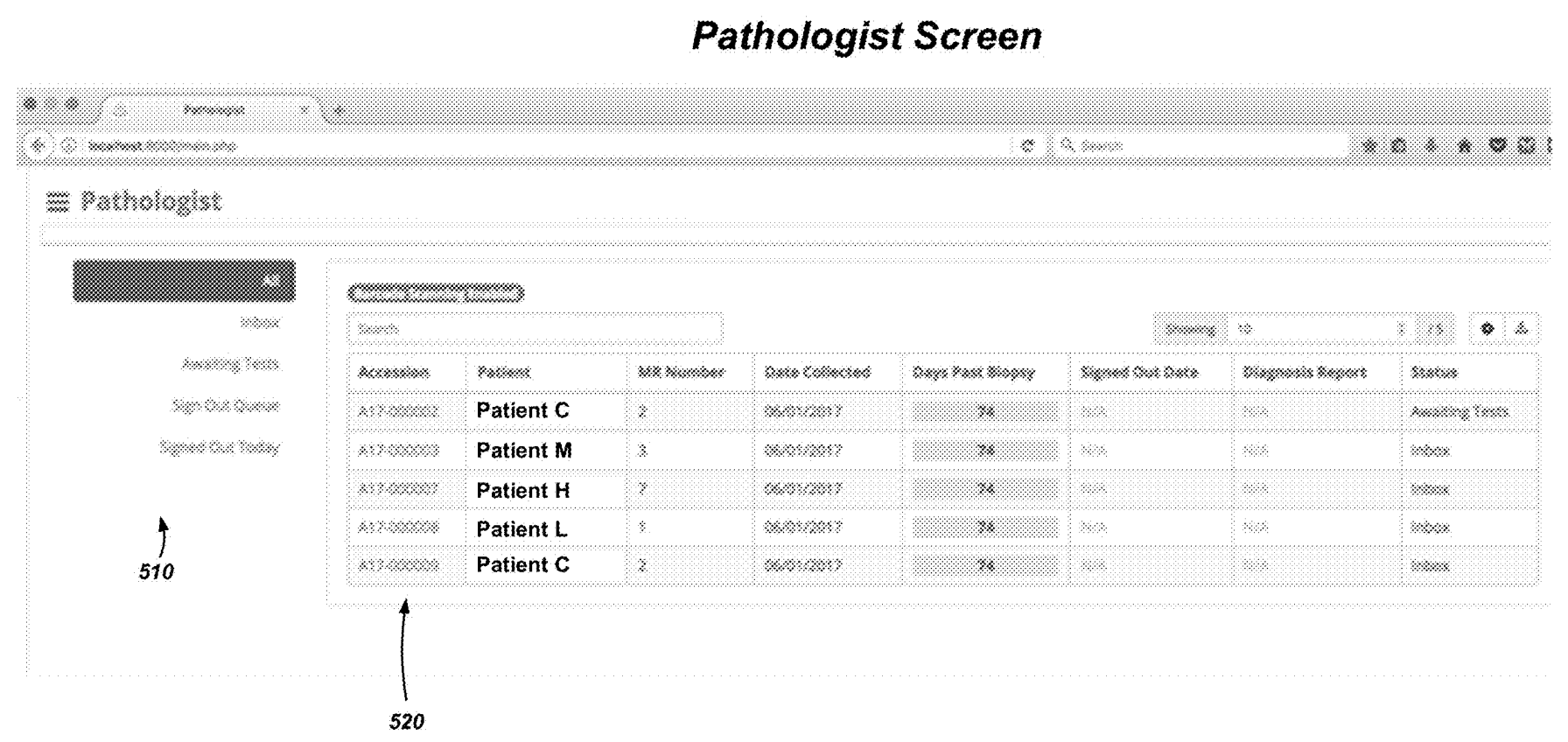

FIG. 5 shows a screenshot of information that may be presented to a Pathologist for editing. In FIG. 5, the screenshot of the application on the client device 210 shows the Pathologist screen where the list of viewing actions 510 the Pathologist can perform and subsequent list of accessions 520 as selected by the action in 510. This screenshot is presented to the Pathologist after logging into the Labdivus system and selecting the Pathologist screen. As a result, the user interface presented may be presented to the specific Pathologist that is logged in and the application software and database 292 may be configured for many Pathologist users. To open up an accession from the accession list 520, the Pathologist clicks on the appropriate accession or, using a barcode reader, scans the accession slide barcode with the accession information contained in it to access the information regarding the specimen, which contains a specific test applied to the tissue on the slide, which is shown to the Pathologist in the screen.

Figure 6:
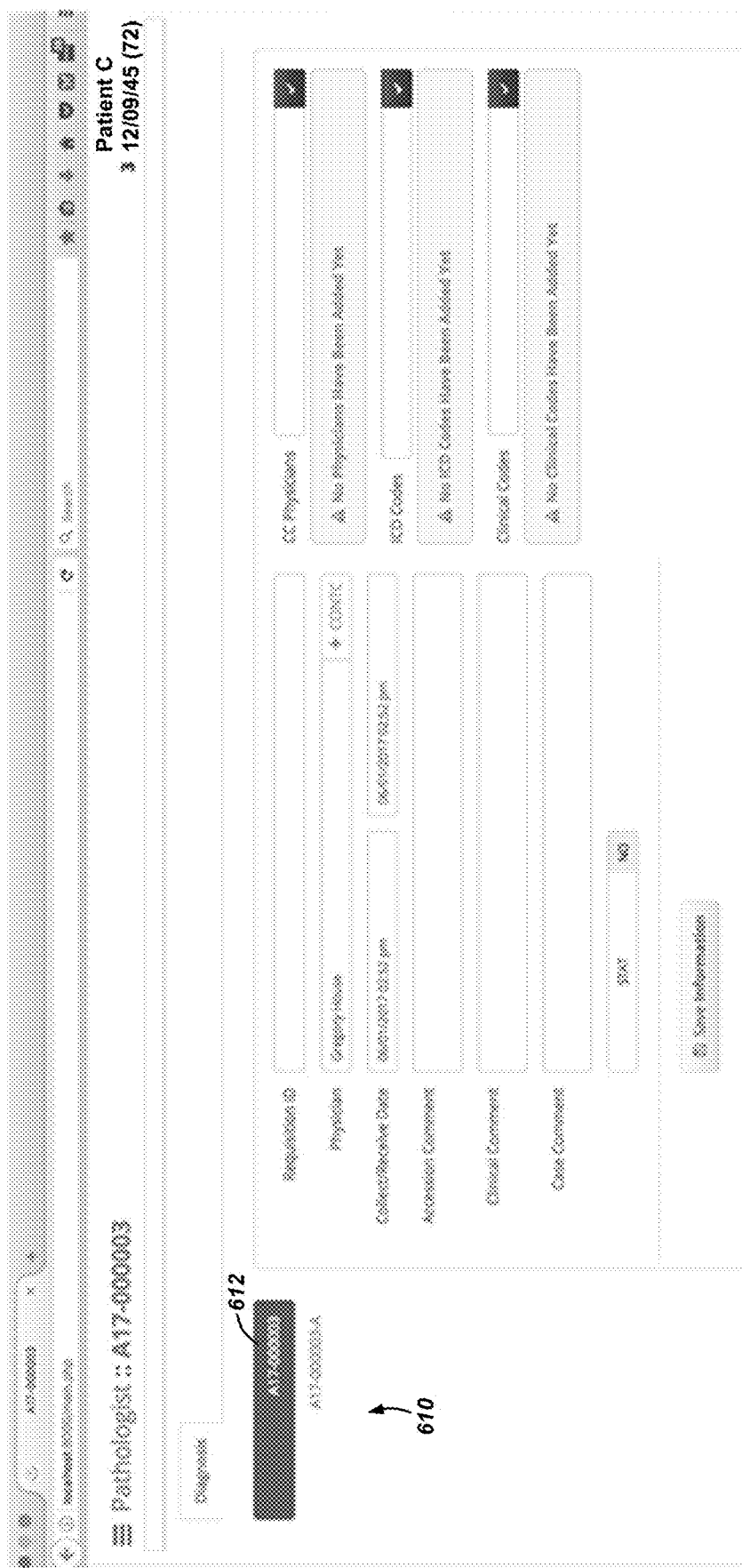
FIG. 6 shows a screenshot of information associated with a specific accession.

FIG. 6 shows a screenshot of information associated with a specific accession that is opened. In FIG. 6, the Pathologist is presented a screen that has a menu 610 on the left side of the screen that shows a main patient component of the accession and a list of associated specimen(s). In this example, one accession specimen (A) 612 is presented in the menu 610. Various informational fields 620 are presented to give the Pathologist details about the selected accession specimen 612. These details may include information such as physician who collected the specimen, collection data, date received at the lab, and various associated comments.

When the Pathologist clicks on the accession specimen 612, the Labdivus web application (i.e., the client portion 230 of the Labdivus application) retrieves the information about the accession and associated specimens from the server portion 280 of the Labdivus application. This method is comprised of a client operation with information sent to the backend server portion of the application that processes the request of getting the data for the specific accession. The Labdivus application utilizes standard HTTP web-based protocols to send and receive information to and from the client device 210. The client side of the application bundles the information about the transaction (i.e. the information about the selected accession specimen) into a JavaScript Object Notation (JSON) format and sends an HTTP operation to the business logic section on the server side. The server portion 280 receives the information, parses the JSON data provided and then accesses the Labdivus application database 292 to retrieve the appropriate information. The database information is kept in several tables of information and a related database function gathers the appropriate data from these table entries. The response data from the database 292 is organized and then constructed into the view model for the Labdivus server 260 to send back to the client device 210 in a data set using an HTML markup language which the client portion 230 decodes and then displays to the Pathologist.

The parent specimen will have one or more tests associated with the specimen and list out the tests that were done on the specimen. The physical slides represent a test applied to the specimen and the Pathologist will read, or view, the slide.

Figure 7:
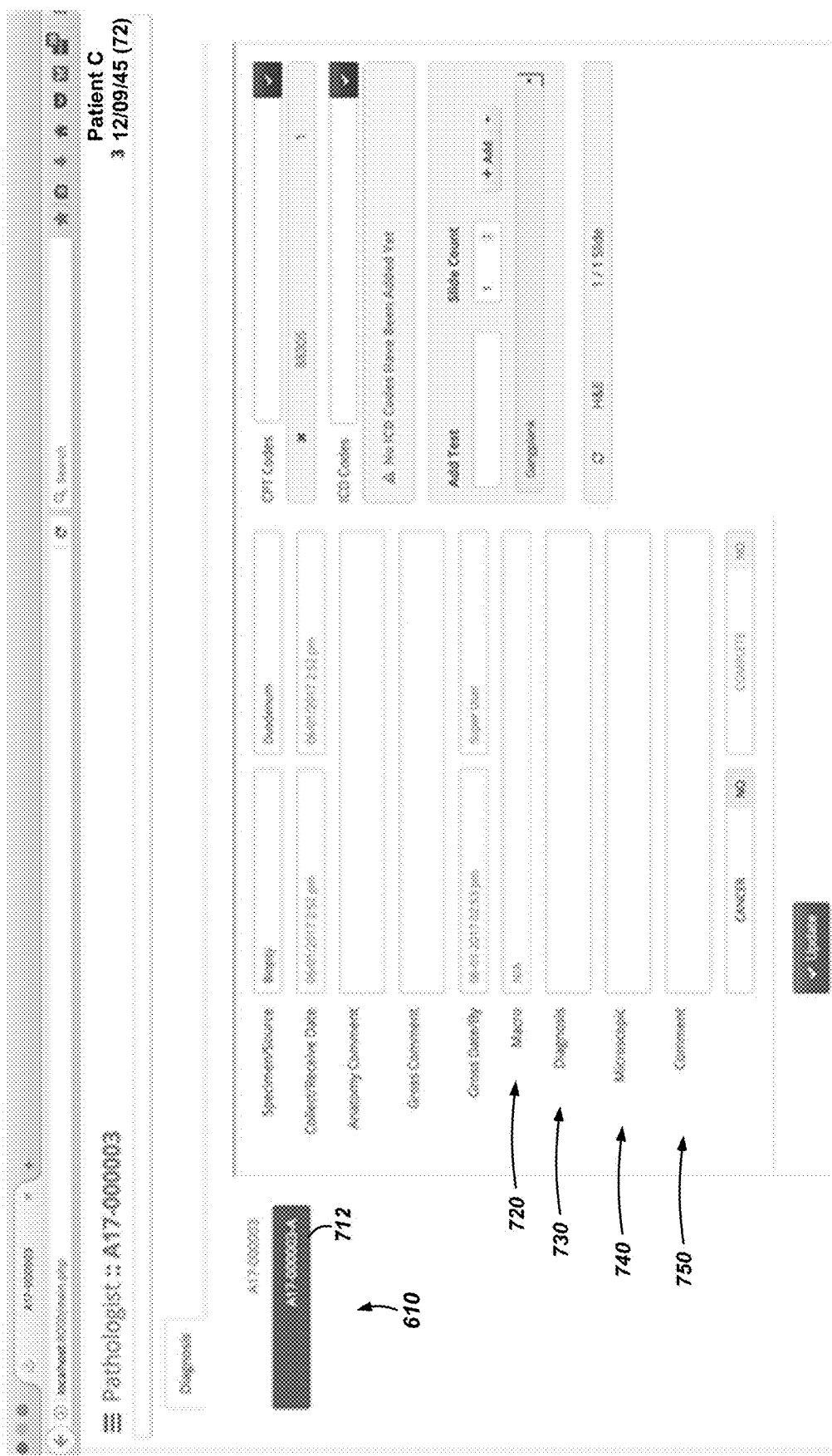
FIG. 7 shows a screenshot of information associated with a specific specimen within a specific accession.

FIG. 7 shows a screenshot of information associated with a specific specimen within a specific accession. The screenshot shows that the accession specimen A 712 is selected from the menu list 610. Various text boxes are included to display information associated with the selected accession specimen 712. In this example details are shown about the specimen and the associated items on the page to enable the Pathologist to enter a diagnosis. Among these items is a selectable combo input box 720 (also referred to herein as a macro entry field 720) with type-into and drop-down menu capabilities to select a particular macro (also referred to herein as a macro name and a macro indicator) based on the initial diagnosis observation from the Pathologist. Macros can be named arbitrarily to help the Pathologist know which macro they are using for the diagnosis. Most Pathologists prefer to name the macro with one or two letters beginning with the anatomy location they are looking at followed by a numbering system based on the details of each type of diagnosis. Other Pathologists can name each macro specifically for the diagnosis short-text of the diagnosis they are using. As a non-limiting example, we will use one letter (A-Z) followed by a series of numbers to identify a particular diagnosis. The application is flexible such that the macro can be comprised of any combination of letters and numbers.

After the Pathologist reads the slide and decides on a diagnosis that should be used, the Pathologist types into the macro entry field 720 or uses the mouse to select a drop-down menu system of all macros available. The list will appear in the macro entry field 720 when the mouse is directed into the area. An auto-fill option in the macro entry field 720 can start narrowing down the macros available based on the characters typed and the user-input can be selected as a drop-down menu. The selected macro will be used and the application then automatically fills in a diagnosis text box area 730 with an initial diagnosis, a microscopic text box area 740, and potentially a comment text box area 750 with the associated text items for each box tied to that macro entered in the macro entry field 720. In other words, the text boxes are pre-populated with information associated with that macro. The communication of the client device 210 to the Labdivus web server portion 280 to retrieve this pre-populated information occurs as similarly described above.

Figure 8:
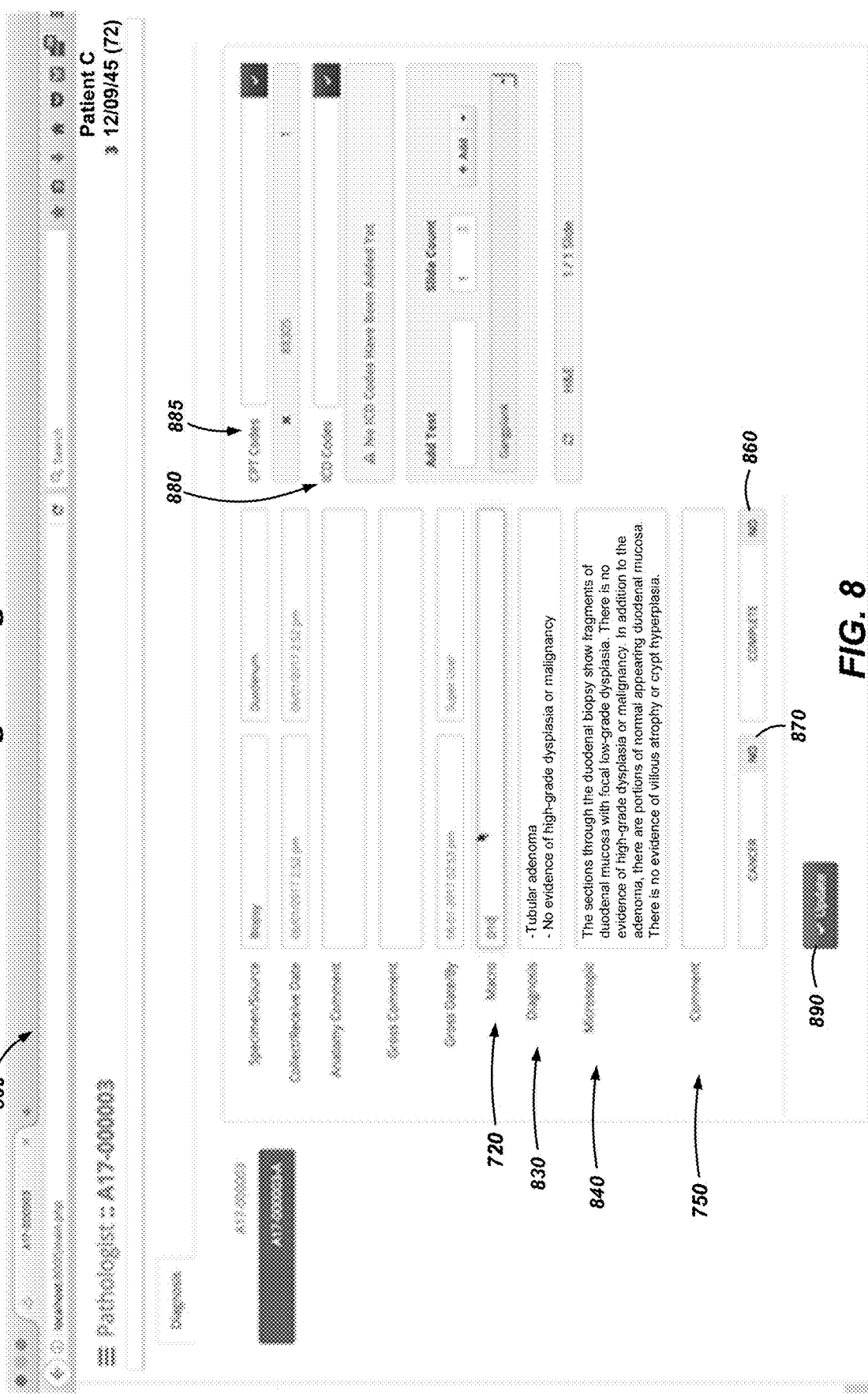
FIG. 8 shows a screenshot with an interface similar to that of FIG. 7, but with some fields populated with macro-based diagnostic suggestions.

FIG. 8 shows a screenshot with an interface similar to that of FIG. 7, but with some fields populated with a macro-based initial diagnosis as suggestions based on the macro indicator entered in the macro entry field 720. Some of these fields that are pre-populated may include the diagnosis text box 730 with an initial suggested diagnosis 830, the microscopic text box 740 with an initial suggested microscope field 840, and the comment text box 750. When the macro is selected, other particular items such as Current Procedural Terminology (CPT) codes 885, International Classification of Diseases (ICD) codes 880, a complete flag 860, and a cancer flag 870 can be set based on the macro selection. By selecting the macro, the Pathologist speeds up input into the Pathology Report for the patient accession about the particular findings for each specimen. To provide a custom diagnosis specific to this specimen, the Pathologist can edit entries in each of the items shown (730, 840, 750, 860, 870, 880, and 885) on the screen after macro selection has pre-populated the items with a macro-specific initial suggested diagnosis 830. An update button 890 may be used to send all the information in the various boxes back to the server 260 to be placed in the database 292 as a modification to the existing macro, or as a new macro entry that can be subsequently selected for future diagnoses.

Figure 9:
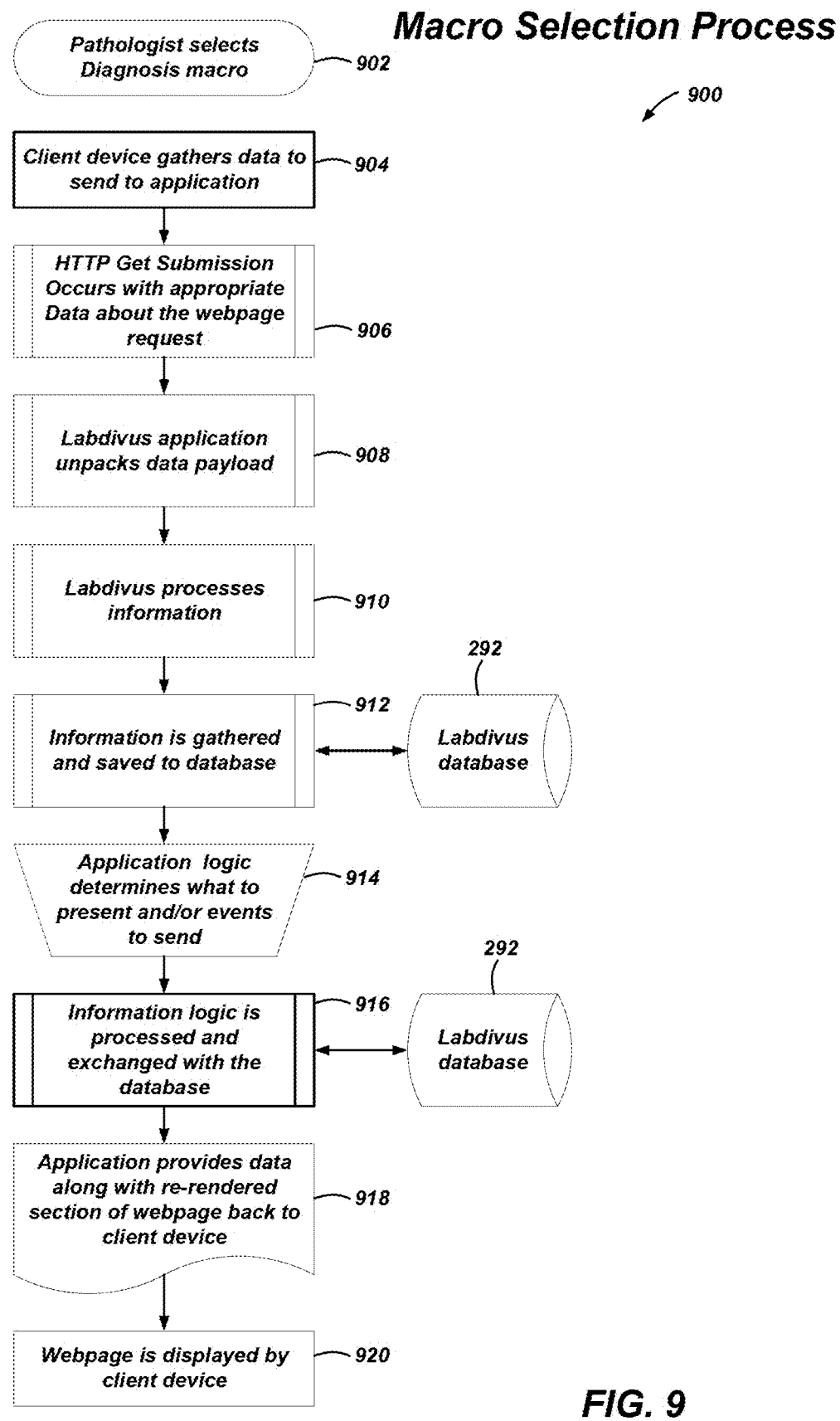
FIG. 9 is a flow chart illustrating some processes of related to macro selection in the application software.

FIG. 9 is a flow chart illustrating a process 900 related to macro selection in the application software. In FIG. 9 the operation of the system flow is shown when the macro selection occurs.

At process block 902, the Pathologist selects the diagnosis macro in the user interface. At process blocks 904 and 906, client device 210 gathers the information and send it through the HTTP protocols through the network to the server 260 running the server portion 280 of the Labdivus application.

At process blocks 908, 910, and 912, the server portion 280 of the Labdivus application unpacks the data, gathers information from the database server 290, and then processes the application data. The application may also exchange data back to the database 292 during this step.

At process blocks 914 the application creates the web page to present with new data and sends it back to the client device 210 for presentation in the user interface.

For example, in the screenshot in FIG. 8 a user has selected D10 for a duodenum diagnosis in the macro entry field 720. The diagnosis text box 830 is pre-populated with the macro-specific initial diagnosis of a tubular adenoma and the microscopic text box 840 is pre-populated with the macro-specific suggested details about the findings. The Pathologist can then edit these items including adding or deleting textual information describing their findings about the specimen. The Pathologist may optionally add new ICD codes 880 or CPT codes 885 or delete any ICD or CPT codes pre-populated by the macro as well for final values. The edited entry 830 in the diagnosis text box 730, the edited entry 840 in the microscopic text box 740, and an edited entry in the comment text 850 are saved for that specimen such that the Pathologist can go back to the case and edit further or finalize, sign, and release the report. If the Pathologist chooses a different macro, the macro system will remove all changes and replace it with a new macro template entry corresponding to the new macro being selected.

At process block 916, 918, and 920, once the Pathologist is done with reviewing all the slides for that specimen, the Pathologist can select the Complete Checkbox 860 which notifies the application that the Pathologist is finished editing this particular specimen. The Pathologist selects the update button 890 to save the changes. When all specimens are completed, the software application generates a final Pathology report with the entered information for each specimen on the report. The report is reviewed by the Pathologist before it is completed with a signout signature. The report can be presented in a text format such as PDF and digitally signed for authentication by the Pathologist signifying a completed report. The signed PDF report will then be distributed by the software application to the appropriate systems for final review.

The software application provides a GUI-based editor so that the Pathologist can create an unlimited numbers of macros for their use in diagnosis. The application supports global macros available to all Pathologists plus each Pathologist can have his or her own set of custom macros in addition to the global ones provided. Each macro can be fully customized to add items into the macro entry field 720, the diagnosis text box 730, the microscopic text box 740, the comment text 850, the ICD code 880, the CPT code 885, and the cancer flag 870. Diagnosis, Microscopic, Comment, CPT, ICD, and Cancer flag fields (820, 840, 850, and 870) on the Pathologist Specimen Diagnosis screen 800.

Pathologists in anatomic pathology laboratories can be varied in their scope of work. For example, some Pathologists are trained as gastroenterology Pathologists dealing with the human digestive system. Others may specialize in urology, dermatology, or oncology. No matter the specialty, each Pathologist in these fields utilize an anatomic pathology laboratory workflow in which the Pathologist would be looking at stained tissue on a slide, deciding a diagnosis based upon their findings and then create a final report that the primary care physician would be reviewing to prescribe any potential treatment for the patient. In the application, the macro-based system used for the particular scope of pathology being done would be utilized by the Pathologist. For example, a gastroenterology lab would have the gastro macros available for the Pathologists. For a urology lab, the macros can be switch to provide specific diagnosis items for urology. This customization allows several different types of pathology to be done on-site or across different types of labs or customers by the application. The application can automatically switch the macros used based upon the type of accession being reviewed. This feature is configurable within the application such that accession (mostly tissue) types will cause the change. For example, dermatology-based specimen diagnoses are very different from gastroenterology or urology. A case that is identified as a dermatology accession will require a different set of macros for diagnosis than the diagnosis for a colon accession. The application utilizes global macros sets identified by the accession (case) type. For each Pathologist, they may have their own custom set of macros for each of these different types (as example, urology, dermatology, gastroenterology) and the application will select the Pathologist-specific set of macros for the appropriate case type. Each Pathologist can have their own set of custom macros that are editable and not shared with other Pathologists. The selection of those macros is user-based and selected when the Pathologist logs into the Labdivus application.

In summary, embodiments of the present disclosure include a server computing system. The server computing system includes one or more processors, memory configured for storing computing instructions, and a database of macro-based diagnoses, each macro-based diagnosis associated with one or more elements of an accession, and one or more specimens associated with the accession and includes at least a field for an initial diagnosis. The computing instructions, when executed on the server computing system, implement a process for generating pathology lab diagnoses. The process is configured to receive a macro indicator from a client device and retrieve the initial diagnosis from the database of macro-based diagnoses responsive to the macro indicator. The process is further configured to transmit the initial diagnosis to the client device, receive an edited version of the initial diagnosis from the client device, and store the edited version of the initial diagnosis in the database of macro-based diagnoses for subsequent retrieval.

Embodiments of the present disclosure also include a client computing system comprising one or more processors and memory configured for storing computing instructions. The computing instructions, when executed on the client computing system, implement a process for generating pathology lab diagnoses. The process is configured to present a user interface to a user, the user interface including a macro entry field for defining a macro indicator from a plurality of macro indicators. The process is further configured to transmit the macro indicator to a server and receive at least an initial diagnosis from the server responsive to the transmission of the macro indicator. The process is also configured to pre-populate a diagnosis text box on the user interface with information from the initial diagnosis and enable the user to edit the entry in the diagnosis text box after it is pre-populated with the initial diagnosis.

Embodiments of the present disclosure also include a computer-implemented method for generating pathology lab diagnoses. The method includes, on a client device, presenting a user interface to a user, the user interface including a macro entry field for defining a macro indicator from a plurality of macro indicators and transmitting the macro indicator. On a server, the method further includes storing a database of macro-based diagnoses, each macro-based diagnosis associated with one or more elements of an accession, and one or more specimens associated with the accession. Also on the server, the method includes receiving the macro indicator from the client device, retrieving an initial diagnosis from the database of macro-based diagnoses responsive to the macro indicator, and transmitting the initial diagnosis. On the client device, the method further includes receiving the initial diagnosis, pre-populating one or more text boxes on the user interface with information from the initial diagnosis, and enabling the user to edit the pre-populated one or more text boxes.

While the disclosure is susceptible to various modifications and implementation in alternative forms, specific embodiments have been shown by way of examples in the drawings and have been described in detail herein. It should be understood that the invention is not limited to the particular forms disclosed. Rather, the invention includes all modifications, equivalents, and alternatives falling within the scope of the following appended claims and their legal equivalents.

What is claimed is:

1. A server computing system, comprising:
   one or more processors;
   memory configured for storing computing instructions; and
   a database of macro-based diagnoses, each macro-based diagnosis associated with one or more elements of an accession, and one or more specimens associated with the accession;
   wherein the computing instructions, when executed on the server computing system, implement a process for generating pathology lab diagnoses, the process configured to:
      provide a plurality of available diagnosis-based macro indicators to a client device, each diagnosis-based macro indicator associated with one of the macro-based diagnoses;

receive a diagnosis-based macro indicator from the client device;
retrieve an initial diagnosis including a macro-based diagnostic suggestion associated with the initial diagnosis from the database of macro-based diagnoses responsive to the diagnosis-based macro indicator;
retrieve a Current Procedural Terminology (CPT) code and an International Classification of Diseases (ICD) code associated with the initial diagnosis responsive to the diagnosis-based macro indicator;
transmit the initial diagnosis including the macro-based diagnostic suggestion to the client device;
transmit the CPT code and the ICD code to the client device to apply the CPT code and the ICD code to the initial diagnosis at a selection time of the diagnosis-based macro indicator;
receive an edited version of the initial diagnosis from the client device including changes to the macro-based diagnostic suggestion; and
store the edited version of the initial diagnosis including the macro-based diagnostic suggestion in the database of macro-based diagnoses for subsequent retrieval.

2. The server computing system of claim 1, wherein:
the database of macro-based diagnoses is further configured to include associations to one or more pathologist users; and
the process is further configured to:
receive the diagnosis-based macro indicator for a specific pathologist of the one or more pathologist users;
retrieve the initial diagnosis from the database of macro-based diagnoses responsive to the diagnosis-based macro indicator for the specific pathologist; and
store the edited version of the initial diagnosis with a relation to the specific pathologist.

3. The server computing system of claim 1, wherein:
the database of macro-based diagnoses is further configured such that each macro-based diagnosis includes additional fields for additional information; and
the process is further configured to:
retrieve the additional information from the database of macro-based diagnoses responsive to the diagnosis-based macro indicator; and
transmit the additional information to the client device.

4. The server computing system of claim 3, wherein the process is further configured to:
receive an edited version of the additional information for at least one of the additional fields; and
store the edited version of the additional information in the database of macro-based diagnoses for subsequent retrieval.

5. The server computing system of claim 4, wherein:
the database of macro-based diagnoses is further configured to include associations to one or more pathologist users; and
the process is further configured to:
receive the diagnosis-based macro indicator for a specific pathologist of the one or more pathologist users;
retrieve the initial diagnosis from the database of macro-based diagnoses responsive to the diagnosis-based macro indicator for the specific pathologist;
retrieve the additional information from the database of macro-based diagnoses responsive to the diagnosis-based macro indicator for the specific pathologist;
store the edited version of the initial diagnosis with a relation to the specific pathologist; and
store the edited version of the additional information with a relation to the specific pathologist.

6. The server computing system of claim 3, wherein the additional fields in the database of macro-based diagnoses include options for CPT codes and options for ICD codes.

7. A client computing system, comprising:
one or more processors; and
memory configured for storing computing instructions;
wherein the computing instructions, when executed on the client computing system, implement a process for generating macro-based diagnoses from a database of macro-based diagnoses for a pathology lab, the process configured to:
present a user interface to a user, the user interface including a diagnosis-based macro entry field for selection by the user of a diagnosis-based macro indicator from a plurality of available diagnosis-based macro indicators, each diagnosis-based macro indicator associated with one of the macro-based diagnoses;
transmit a selected diagnosis-based macro indicator to a server;
receive at least an initial diagnosis including a macro-based diagnostic suggestion associated with the initial diagnosis from the server responsive to the transmission of the selected diagnosis-based macro indicator;
receive a Current Procedural Terminology (CPT) code and an International Classification of Diseases (ICD) code associated with the initial diagnosis responsive to the transmission of the selected diagnosis-based macro indicator;
pre-populate a diagnosis text box on the user interface with the macro-based diagnostic suggestion;
populate a CPT code selection field and an ICD code selection field with the received CPT code and the ICD code at a selection time of the selected diagnosis-based macro indicator; and
enable the user to edit an entry in the diagnosis text box after it is pre-populated with the macro-based diagnostic suggestion.

8. The client computing system of claim 7, wherein the process is further configured to transmit the edited entry from the diagnosis text box to the server for storing in the database of macro-based diagnoses where it is available for subsequent retrieval.

9. The client computing system of claim 7, wherein the process is further configured to:
receive additional information from the server responsive to the selected diagnosis-based macro indicator;
pre-populate one or more additional text boxes on the user interface with the additional information; and
enable the user to edit the one or more additional text boxes.

10. The client computing system of claim 9, wherein the process is further configured to transmit edited text in the one or more additional text boxes to the server for storing in the database of macro-based diagnoses where it is available for subsequent retrieval.

11. The client computing system of claim 9, wherein the one or more additional text boxes include text boxes for microscopic text and comment text.

12. The client computing system of claim 7, wherein the user interface is further configured to enable a user to:
add new CPT codes, ICD codes, or both to the CPT code selection field and the ICD code selection field; and
delete CPT codes, ICD codes, or both from the CPT code selection field and the ICD code selection field.

13. A computer-implemented method for generating pathology lab diagnoses, comprising:
on a client device:
presenting a user interface to a user, the user interface including:
a macro entry field for selection by the user of a diagnosis-based macro indicator from a plurality of available diagnosis-based macro indicators; and
one or more text boxes; and
transmitting the diagnosis-based macro indicator;
on a server:
storing a database of macro-based diagnoses, each macro-based diagnosis associated with one or more elements of an accession, and one or more specimens associated with the accession;
receiving the diagnosis-based macro indicator from the client device;
retrieving an initial diagnosis including a macro-based diagnostic suggestion associated with the initial diagnosis from the database of macro-based diagnoses responsive to the diagnosis-based macro indicator;
retrieving a Current Procedural Terminology (CPT) code and an International Classification of Diseases (ICD) code associated with the initial diagnosis responsive to the diagnosis-based macro indicator;
transmitting the CPT code and the ICD code; and
transmitting the initial diagnosis including the macro-based diagnostic suggestion; and
on the client device:
receiving the initial diagnosis including the macro-based diagnostic suggestion;
receiving the CPT code and the ICD code;
pre-populating at least one of the one or more text boxes on the user interface with information including the macro-based diagnostic suggestion;
populating a CPT code selection field and an ICD code selection field with the received CPT code and the ICD code at a selection time of the diagnosis-based macro indicator; and
enabling the user to edit the pre-populated at least one of the one or more text boxes.

14. The computer-implemented method of claim 13, wherein the pre-populated at least one of the one or more text boxes include a diagnosis text box and is pre-populated with the initial diagnosis.

15. The computer-implemented method of claim 14, further comprising enabling the user to customize the initial diagnosis in the diagnosis text box.

16. The computer-implemented method of claim 15, further comprising transmitting the customization of the initial diagnosis from the client device to the server and storing a customized diagnosis in the database of macro-based diagnoses.

17. The computer-implemented method of claim 13, wherein the pre-populated one or more text boxes include text boxes for microscopic text and comment text.

18. The computer-implemented method of claim 17, further comprising enabling the user to customize the microscopic text and the comment text.

19. The computer-implemented method of claim 18, further comprising transmitting the customization of the microscopic text and the comment text from the client device to the server and storing the customized entries in the database of macro-based diagnoses.

20. The computer-implemented method of claim 13, wherein the user interface is further configured to enable the user to:
add new CPT codes, ICD codes, or both to the CPT code selection field and the ICD code selection field;
delete CPT codes, ICD codes, or both from the CPT code selection field and the ICD code selection field; and
replace previously populated CPT codes, previously populated ICD codes, or both from the one CPT code selection field and the ICD code selection field.

* * * * *